(12) United States Patent
Motoki

(10) Patent No.: US 7,162,067 B2
(45) Date of Patent: Jan. 9, 2007

(54) IMAGE READING SYSTEM AND METHOD FOR RADIOGRAPHY WITH PREREGISTRATION AND POST-REGISTRATION OPTIONS

(75) Inventor: Wataru Motoki, Hino (JP)

(73) Assignee: Konica Corporation (JP)

( * ) Notice: Subject to any disclaimer, the term of this patent is extended or adjusted under 35 U.S.C. 154(b) by 790 days.

(21) Appl. No.: 10/336,574

(22) Filed: Jan. 3, 2003

(65) Prior Publication Data

US 2003/0142858 A1 Jul. 31, 2003

(30) Foreign Application Priority Data

Jan. 31, 2002 (JP) ............... 2002-023351

(51) Int. Cl.
*G06K 9/00* (2006.01)
*H05G 1/58* (2006.01)

(52) U.S. Cl. .............. 382/132; 378/115; 378/165

(58) Field of Classification Search ........ 378/114, 378/115, 116, 162, 165; 382/128, 132
See application file for complete search history.

(56) References Cited

U.S. PATENT DOCUMENTS

| | | | | |
|---|---|---|---|---|
| 3,859,527 | A | | 1/1975 | Luckey .................. 250/327 |
| 4,739,480 | A | * | 4/1988 | Oono et al. ............ 364/414 |
| 5,334,851 | A | * | 8/1994 | Good et al. ........... 250/582 |
| 5,694,450 | A | * | 12/1997 | Livingston ............. 378/166 |
| 2001/0011713 | A1 | * | 8/2001 | Nagatsuka et al. ...... 250/584 |

FOREIGN PATENT DOCUMENTS

| | | |
|---|---|---|
| JP | 55-12144 A | 1/1980 |
| JP | 63-253348 A | 10/1998 |
| JP | 11-289426 A | 10/1999 |

OTHER PUBLICATIONS

Notice of Reason for Rejection to JP patent Application No. 2002-023351 with partial English translation of marked up portion.

* cited by examiner

*Primary Examiner*—Andrew W. Johns
(74) *Attorney, Agent, or Firm*—Cantor Colburn LLP

(57) ABSTRACT

The invention is designed to help coordinate the processing of radiographic images for a lab, hospital, office, or other locations for example. The image reading system may have a reading device for reading image information from a containing member in which a recording medium capable of recording a radiographic image is built. The control device may set a reading condition of the containing member. An ID giving section may provide ID information to one of the containing member and the recording medium. A storage section may store the reading condition. A selecting section may select at least one of a first registration type and a second registration type, the first registration type being for registering a correspondence between the reading condition and the containing member or the recording medium before image recording and the second registration type being for registering the correspondence after the image recording, and for using the system on a basis of the selected registration type. A control section may correlate the reading device, the ID giving section, the control device, and the storage section.

19 Claims, 15 Drawing Sheets

IMAGE READING SYSTEM AND METHOD FOR RADIOGRAPHY WITH PREREGISTRATION AND POST-REGISTRATION OPTIONS

BACKGROUND OF THE INVENTION

1. Field of the Invention

The present invention relates to an image reading system and method, particularly to a system and method usable irrespective of order of radiographing and input of reading conditions of radiographed image data.

2. Description of Related Art

An image obtained by using radiation, such as X-ray or the like, has been known widely as a medical image for diagnosing diseases. For example, so-called X-ray photograph by which development is performed by irradiating the X-ray transmitted through a subject to a phosphor layer (phosphor screen) and irradiating the visible light generated in the phosphor layer to a film, in which silver salts are used as the same as usual photograph, has been used in earlier technology.

However, recently, a method for taking out an image directly from a phosphor layer has been used instead of a film coated with silver salts. This method is a method for obtaining image signals explained as follows. That is, after the X-ray transmitted through a subject is absorbed into a phosphor, the phosphor layer is excited by light or heat and X-ray energy accumulated in the phosphor layer is emitted as a fluorescence light. Then, the fluorescence light is converted photoelectrically into image signals.

Concretely, for example, an X-ray image converting method in which a stimulating phosphor is used and visible rays or infrared rays are used as stimulating excitation lights is disclosed in the U.S. Pat. No. 3,859,527 and the Japanese Patent Laid-Open Publication No. 55-12144. In this method, a radiographic image converting plate in which a stimulating phosphor layer is formed on a supporting member is used. The X-ray transmitted through a subject is irradiated to this stimulating phosphor layer, and a latent image is formed by accumulating the X-ray energy corresponding to the quantity of X-ray transmitted through each body part of the subject. Thereafter, the stimulating phosphor layer is scanned by a stimulating excitation light, such as laser beam having a predetermined wavelength or the like, and the accumulated X-ray energy is emitted as a stimulating light. Then, the stimulating light is converted photoelectrically into electric signals by using a photoelectric transducer, such as photomultiplier or the like, and the electric signals are taken out.

The X-ray image radiographing utilizing the stimulating phosphor can be roughly classified into two types. One is a exclusive type that a radiographic image converting plate is fixed, and the other is a cassette type that a cassette containing a radiographic image converting plate in the inside thereof and capable of being carried is used. The X-ray image radiographing of the above-described cassette type will be explained with reference to FIG. 17.

As shown in FIG. 17, the X-ray image radiographing of the above-described cassette type is performed by a system including a cassette 110 capable of being carried, in which a radiographic image converting plate having a stimulating phosphor sheet 130 for accumulating X-ray energy is built, a reader 200 for reading an X-ray image from the cassette 110, and a controller 300 for controlling the reader 200 and performing display and input.

Then, a subject M is located between an X-ray source 140 and the cassette 110, and an X-ray is irradiated from the X-ray source 140. The stimulating phosphor sheet 130 in the cassette 110 accumulates a part of irradiated radiation energy. Then, when this cassette 110 is set in the reader 200, an excitation light is irradiated to the stimulating phosphor sheet 130 in order to read out the X-ray image information accumulated in the stimulating phosphor sheet 130 in the cassette 110, in the reader 200. Then, the stimulating light body which emits a light in accordance with the X-ray image information accumulated by the irradiated excitation light is converted photoelectrically, and A/D conversion is carried out. Thereafter, the reader 200 outputs it as digital image data.

Further, the controller 300 performs the control of reading of the reader 200, and also has a monitor for inputting the order information, such as patient information, body parts for radiographing and the like, and for confirming the read image. In order to deal with various workflows, there have been many cases such that the reader 200 and its exclusive controller 300 are installed in one or a set of the reader 200 and its exclusive controller 300 being connected separately by 1 to 1 are installed in an X-ray room.

However, high accuracy is required for these systems since they are used in medical diagnosis, so that the cost is extremely high. Therefore, it is noneconomic to install a reader 200 and controller 300 regardless of frequency of radiographing in a radiographing room, and furthermore, the installation space becomes large. Thereby, there are many cases that the reader 200 and controller 300 are installed only in the radiographing room of high frequency of radiographing. In such a constitution, in case that radiographing is performed in a radiographing room in which the above-described set is not installed, the cassette 110 is carried into the radiographing room at first, and after radiographing is performed, the cassette 110 is moved into the radiographing room in which a reader 200 is installed in order to read the radiographed X-ray image. Thereby, there is a possibility that the correspondence between the cassette 110 and the patient may become unclear when radiographing is performed to many patients among many radiologists.

Further, the time after going to the reader 200 from the radiographing room, setting the cassette 110 and confirming the image until returning to the radiographing room becomes long. Therefore, there is a problem such that the burden to patients becomes large since the radiographing time becomes long, or the like.

Then, in order to make the correspondence between the cassette 110 and the reading conditions of a radiographic image converting plate clear even though it is the case that radiographing of the X-ray image and reading take place in different places, a method for performing radiographing after registering the correspondence between the cassette 110 and the reading conditions of the radiographic image converting plate beforehand (hereinafter, the method for performing radiographing after registering the correspondence is called "pre-registration") has been used. The procedure according to the pre-registration type will be explained in the following.

In this method, the order information, such as body parts for radiographing, sensitivity, resolution and the like, are inputted by the controller 300, input terminal or the like. At the same time, the ID information of an identification label for identifying the stimulating phosphor sheet 130 contained in the cassette 110 is read, and is registered in a database through a network as information by being made to correspond to the sensitivity, resolution. Then, radiographing is carried out to a patient by using the registered cassette 110. Thereafter, the cassette 110 is set in the reader 200, and the ID information of the stimulating phosphor sheet 130 is read by an identification label detector which is connected to or built in the reader 200. The reader 200 refers to the database by making the read ID information search key, and obtains the address of the controller 300 in which the sensitivity, resolution and the reading conditions of the radiographic image converting plate are registered, from the database. Then, the X-ray image information accumulated in the stimulating phosphor sheet 130 is read by using the sensitivity and resolution, and the reader 200 sends the ID information and the X-ray image information to the controller 300 of the obtained address. The controller 300 receives the ID information and the X-ray image information from the reader 200, and specifies the reading conditions of the radiographic image converting plate from the ID information. Then, the controller 300 determines the image processing method from the body parts for radiographing, performs the image processing, and displays the image.

According to the system using this method, it is possible to connect a plurality of readers 200 and controllers 300 in a network. Further, the installation space can be made small by installing only the controller 300 in each radiographing room in a hospital and by installing a plurality of readers 200 in a common space among the radiographing rooms.

The above-described system adopting the pre-registration is effective in a mode that many radiologists perform radiographing to many patients, such as in a large hospital or the like, since the installation space of the readers 200 and controllers 300 can be made small. However, in case that one or few radiologist performs radiographing in one radiographing room, such as in a clinic or the like, there is a problem that operation becomes complicated on the contrary since the correspondence between the reading conditions, such as sensitivity, resolution and the like, and the ID information of the cassette 110 has to be registered at every radiographing even though the correspondence between the cassette 110 and the patient is clear. Further, in case in a large hospital, there is a problem that quick procedure cannot be carried out since registration of a cassette 110 beforehand is required even though when radiographing must be performed immediately, such as in emergency or the like.

Then, the inventor suggests a registering method which can make the correspondence between a cassette 110 and the reading conditions of a radiographic image converting plate clear without performing the registration of the cassette 110 before radiographing (hereinafter, the type which the correspondence is registered after radiographing is called "post-registration") in the earlier Japanese Patent Laid-Open Publication No. 11-289426. The outline of the technology in the above-described Publication will be explained.

In the post-registration type, the order information (sensitivity and resolution of reading conditions of a radiographic image converting plate, patient information, body parts for radiographing and the like) are inputted by a controller 300 or input terminal after radiographing is performed. Then, the sensitivity and resolution of the reading conditions of the radiographic image converting plate and the ID which shows that it is post-registration (ID for post-registration) are made to correspond, and are registered in a database through a network by taking the input order into consideration. Then, when the cassette 110 is inserted into the reader 200, the reader 200 refers to the database by using the ID information for post-registration, and obtains the address of the controller 300 in which the sensitivity, resolution and the reading conditions of the radiographic image converting plate are registered in accordance with the correspondence between the input order of the reading conditions of the radiographic image converting plate and the insertion order of the cassette 110. Thereafter, the X-ray image information accumulated in the stimulating phosphor sheet 130 in the cassette 110 is read by using this sensitivity and resolution, and the reader 200 sends the ID information and the read X-ray image information to the controller 300 of the obtained address. The controller 300 receives the ID information and the X-ray image information from the reader 200, and specifies the order information from the reception order. Then, the controller 300 determines the image processing method from the body parts for radiographing, performs the image processing, and displays the image.

In the post-registration type, it is not required to register the correspondence between the reading conditions of the radiographic image converting plate, such as sensitivity, resolution and the like, and the ID information of a cassette 110 before radiographing. Therefore, in case that one radiologist performs radiographing in one radiographing room, such as in a clinic or the like, the efficiency of operation can be improved. Further, since radiographing can be performed immediately in an emergency, quick procedure becomes possible.

Thus, in a hospital in which many readers 200 and controllers 300 are installed in different places, respectively, and many radiologists perform radiographing, or the like, radiographing of many patients can be performed effectively according to the pre-registration. On the other hand, in a clinic in which the number of installed readers 200 and controllers 300 is small and a few radiologists perform radiographing, or the like, radiographing can be performed quickly and effectively according to the post-registration. However, only one of registration types can be utilized. Therefore, for example, there is a problem such that quick radiographing cannot be performed in an emergency in a hospital, or that inconvenience may be caused when expanding the system by extending the readers 200 or controllers 300 in a clinic.

SUMMARY OF THE INVENTION

The present invention was made in view of the above-described problems. A main object of the present invention is to provide an image reading system and method capable of setting and changing appropriately and quickly the registration type, which is pre-registration or post-registration type, in accordance with the installed number and installation mode of readers and controllers.

In order to solve the above-described problems, according to a first aspect of the present invention, the image reading system of the present invention comprises: an image reading apparatus having a reading device for reading image information from a containing member in which a recording medium capable of recording a radiographic image is built, and a control device for setting a reading condition of the containing member; a storage section for storing the reading condition; a selecting section for selecting at least one of a first registration type and a second registration type, the first registration type being for registering a correspondence between the reading condition and the containing member or the recording medium before image recording and the second registration type being for registering the correspondence after the image recording, and for using the image reading apparatus on a basis of the selected registration type; an ID giving section for giving ID information for the first registration type or the second registration type to one of the containing member and the recording medium in accordance with the selected registration type; a connecting section for making the reading condition and the ID information correspond in accordance with the selected registration type; and a control section for controlling the reading device so as to read the image information on the basis of the reading condition which is made to correspond by the connecting section according to the ID information given to one of the containing member and the recording medium when reading the image information from the containing member.

According to the image reading system of the present invention, since the reading condition is capable of being correspond by using the ID information for the first and second registration types, the first and the second registration types can be selected appropriately in accordance with the utilizing mode of the installed number and installation mode of the reading device and control device in the image reading apparatus and work-flow of a hospital or a clinic. Therefore, the image information can be read according to either registration type. Thus, since the same devices, such as reading device, control device and the like, can be applied to both registration types, which is the first registration type and the second registration type, it is unnecessary to change the devices to other ones and connections between devices when changing the registration type. Therefore, changing from one registration type to the other registration type can be carried out easily.

In the image reading system, preferably, the ID information for the first registration type is provided on one of the containing member and the recording medium, and when the first registration type is selected, the reading condition is stored in the storage section by being made to correspond to the ID information for the first registration type before the image recording, and the ID information for the first registration type is read by the reading device after the image recording, and the image information is read by searching the reading condition on the basis of the read ID information for the first registration type, and when the second registration type is selected, the reading condition is made to correspond to the ID information for the second registration type and stored in the storage section in input order after the image recording, and the image information is read by searching the reading condition from a correspondence between the input order of the ID information for the second registration type and of the reading condition and an image reading order of the containing member in the reading device.

Further, according to a second aspect of the present invention, the image reading system of the present invention comprises: a reading device for reading image information from a containing member in which a recording medium capable of recording a radiographic image is built; a control device for setting a reading condition of the containing member; an ID giving section for giving ID information to one of the containing member and the recording medium; a storage section for storing the reading condition; a selecting section for selecting at least one of a first registration type and a second registration type, the first registration type being for registering a correspondence between the reading condition and the containing member or the recording medium before image recording and the second registration type being for registering the correspondence after the image recording, and for using the system on a basis of the selected registration type; and a control section for correlating the reading device, the ID giving section, the control device, and the storage section.

According to the image reading system of the present invention, the first and the second registration types can be selected appropriately in accordance with the utilizing mode of the installed number and installation mode of the reader and controller in the image reading apparatus. Therefore, the image information can be read according to either registration type.

In the image reading system, preferably, when the first registration type is selected, the ID information is given as ID information for the first registration type, and the ID information for the first registration type is provided on one of the containing member and the recording medium, and the reading condition is stored in the storage section by being made to correspond to the ID information for the first registration type before the image recording, and the ID information for the first registration type is read by the reading device after the image recording, and the image information is read by searching the reading condition on the basis of the read ID information for the first registration type, and when the second registration type is selected, the ID information is given as ID for the second registration type, and the reading condition is made to correspond to the ID information for the second registration type and stored in the storage section in input order after the image recording, and the image information is read by searching the reading condition from a correspondence between the input order of the ID information for the second registration type and of the reading condition and an image reading order of the containing member in the reading device.

Alternatively, the ID information may be provided on one of the containing member and the recording medium, and when the first registration type is selected, the reading condition may be stored in a first saving section of the storage section by being made to correspond to the ID information before the image recording, and the ID information may be read by the reading device after the image recording, and the image information may be read by searching the reading condition on the basis of the read ID information, and when the second registration type is selected, a second registration type index may be added to the ID information, and the reading condition may be stored in a second saving section of the storage section by being made to correspond to the ID information to which the second registration type index is added after the image recording, and thereafter, the image information may be read by searching the reading condition on the basis of the read ID information to which the second registration type index is added.

Further, a control device having a function of giving the ID information, and a function of setting the reading condition of the containing member may be provided. Moreover, the control device or the reading device is preferable to comprise a function of displaying the read image information. In addition, the reading device is preferable to comprise a function of giving the ID information.

Furthermore, the selecting section may make the first registration type and the second registration type coexist in the image reading system. Thereby, a mode such that the first and second registration types are coexisting can be applied.

Further, it is preferable that at least one of the control device and the ID giving section comprises a specifying section for specifying a destination to deliver the read image information. The radiographic image may be, for example, an X-ray image, and the ID information for the first registration type may be a barcode.

Moreover, the image reading system may comprise a plurality of the reading devices and the control devices. In this case, the control section is preferable to make the image reading system capable of being used by making the first registration type and the second registration type coexist. Further, the reading devices and the control devices are preferable to be correlated by 1:1 when the second registration type is selected.

Further, according to a third aspect of the present invention, the image reading method of the present invention is the method for reading image information from a containing member in which a recording medium capable of recording a radiographic image is built, comprising: selecting at least one of a first registration type and a second registration type, the first registration type being for registering a correspondence between the reading condition and the containing member or the recording medium before image recording and the second registration type being for registering the correspondence after the image recording; and giving ID information to one of the containing member and the recording medium.

In the image reading method, preferably, the ID information is given in accordance with the selected registration type, and when the first registration type is selected, the ID information is given as ID information for the first registration type, and when the second registration type is selected, the ID information is given as ID for the second registration type, and in the first registration type, the method comprises: registering the reading condition and the ID information for the first registration type by making them correspond before the image recording; reading the ID information for the first registration type after the image recording; and controlling reading of the image information by searching the reading condition on a basis of the read ID information for the first registration type; and in the second registration type, the method comprises: registering the reading condition and the ID information for the second registration type in input order by making them correspond before the image recording; and controlling reading of the image information by searching the reading condition from a correspondence between registration order of the reading condition and image reading order of the containing member. In this case, in the second registration type, the reading of the image information is preferable to be carried out after the reading condition and the ID information for the second registration type are registered.

Alternatively, in the first registration type, the method may comprise: registering the reading condition and the ID information in a first saving section by making them correspond before the image recording; reading the ID information after the image recording; and controlling reading of the image information by searching the reading condition from the first saving section on a basis of the read ID information; and in the second registration type, the method may comprise: adding a second registration type index to the ID information; registering the reading condition and the ID information to which the second registration type index is added in a second saving section by making them correspond after the image recording; reading the ID information after the registering; and controlling reading of the image information by searching the reading condition from the second saving section on the basis of the read ID information to which the second registration index is added.

Moreover, the method may further comprise: adding information for specifying a device to send the read image information, when the reading condition is registered; and sending the read image information to the specified device.

Further, the reading of the image information may be carried out by an image reading apparatus having a reading device for reading the image information, and a controlling device. In case of a plurality of the image reading apparatuses, the selection of the first registration type and the second registration type may be carried out on each of the image reading apparatuses. Moreover, the image reading method may further comprise: storing corresponding information between at least one of the reading device and the control device, and the first and second registration types, and at least one of the first registration type and the second registration type may be selected with reference to the corresponding information when at least one of the reading device and the control device is actuated.

Furthermore, preferably, the reading condition includes information of sensitivity and resolution.

BRIEF DESCRIPTION OF THE DRAWINGS

The present invention will become more fully understood from the detailed description given hereinbelow and the appended drawings which given by way of illustration only, and thus are not intended as a definition of the limits of the present invention, and wherein.

PREFERRED EMBODIMENT OF THE INVENTION

In a preferred embodiment, the image reading system according to the present invention comprises a reader (reading device) for reading image data (image information) from a radiographic image converting plate (recording medium) in which an X-ray image (radiographic image) is recorded as a latent image, a controller (control device) for inputting reading conditions of the radiographic image converting plate and for controlling reading of the reader, a job manager (storage section, control section) for storing corresponding information between each device and registration type or corresponding information between the ID (ID information) registered in case of pre-registration (first registration type) or post-registration (second registration type) and the reading conditions, and for searching by using a predetermined key. The reader, controller, and job manager are connected to each other. The registration type of the controller or reader is set beforehand at the time of start-up by using the corresponding information between each apparatus and the registration type. When the reader and controller are set in the pre-registration type, the job manager searches the reading conditions by making a plate ID (ID information for the first registration type) a key. When the reader and controller are set in the post-registration type, the reading conditions are searched from the correspondence between the input order of the reading conditions and the insertion order of a cassette (containing member) by using an ID for post-registration (ID information for the second registration type). Thereby, the system can correspond to either registration type, and further, reading processing can be performed even though it is a case that both registration types are coexisting.

The embodiments of the present invention will be explained in detail with reference to the drawings.

[First Embodiment]

Figure 1:
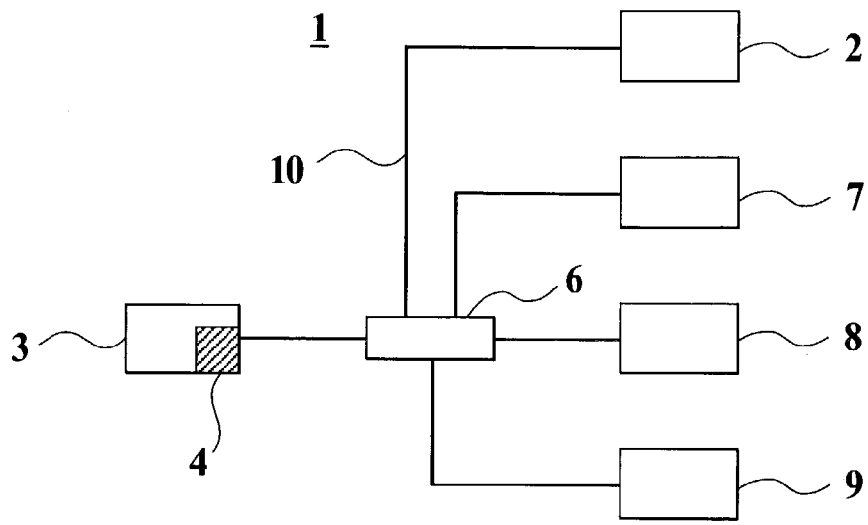
FIG. 1 is a block diagram schematically showing a construction of an X-ray imaging system according to a first embodiment of the present invention.
Figure 2:
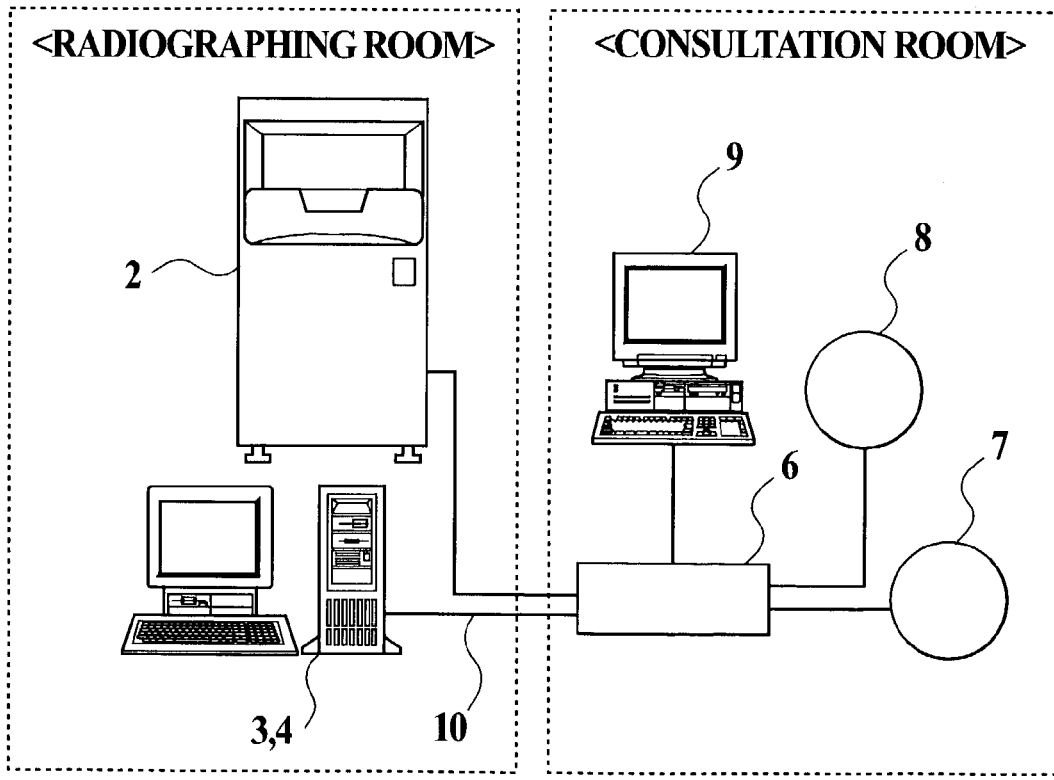
FIG. 2 is a block diagram schematically showing a construction of the X-ray imaging system according to the first embodiment of the present invention in every installation place.
Figure 3:
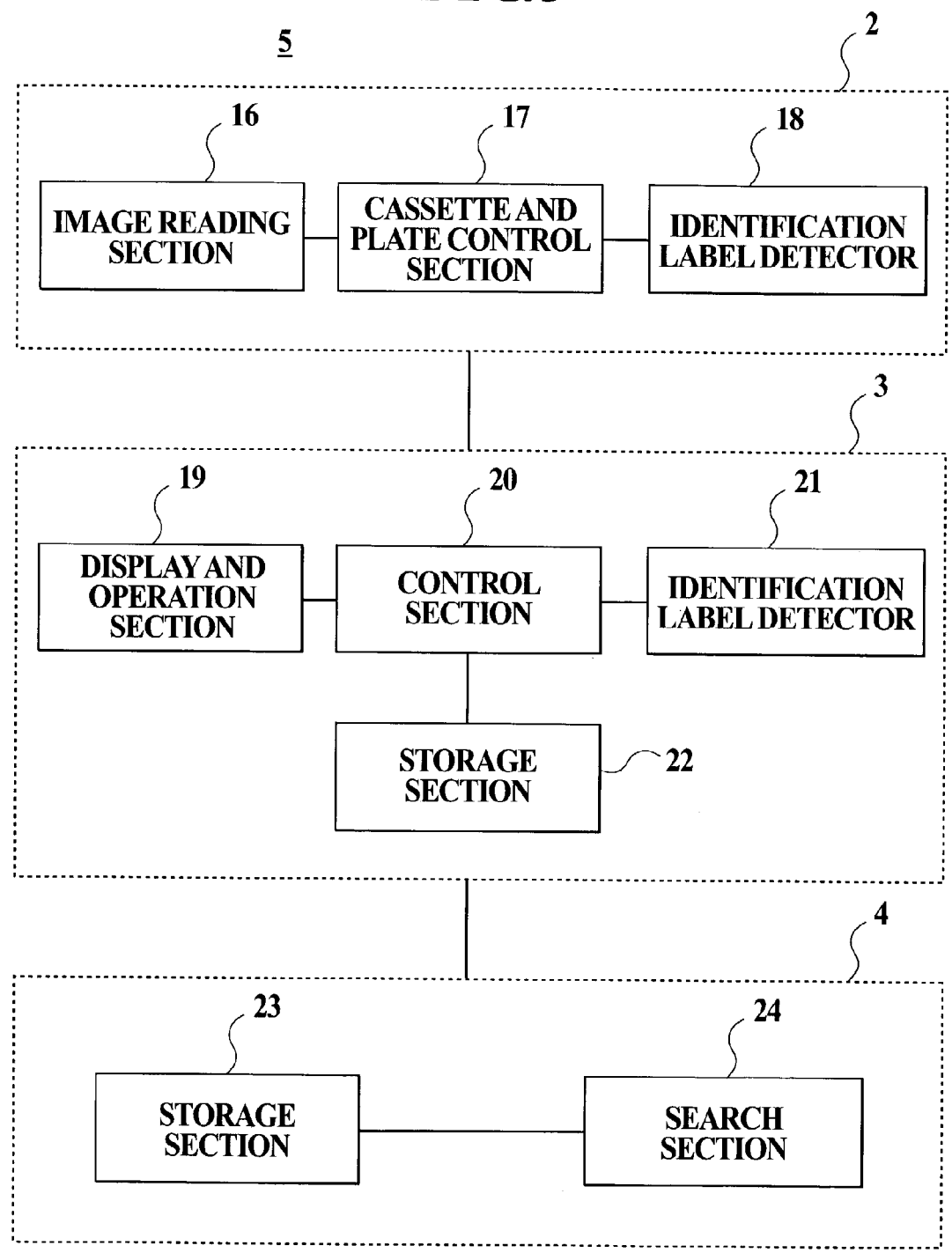
FIG. 3 is a block diagram showing a function of an image reading apparatus (reader, controller and job manager) according to the first embodiment of the present invention.
Figure 4:
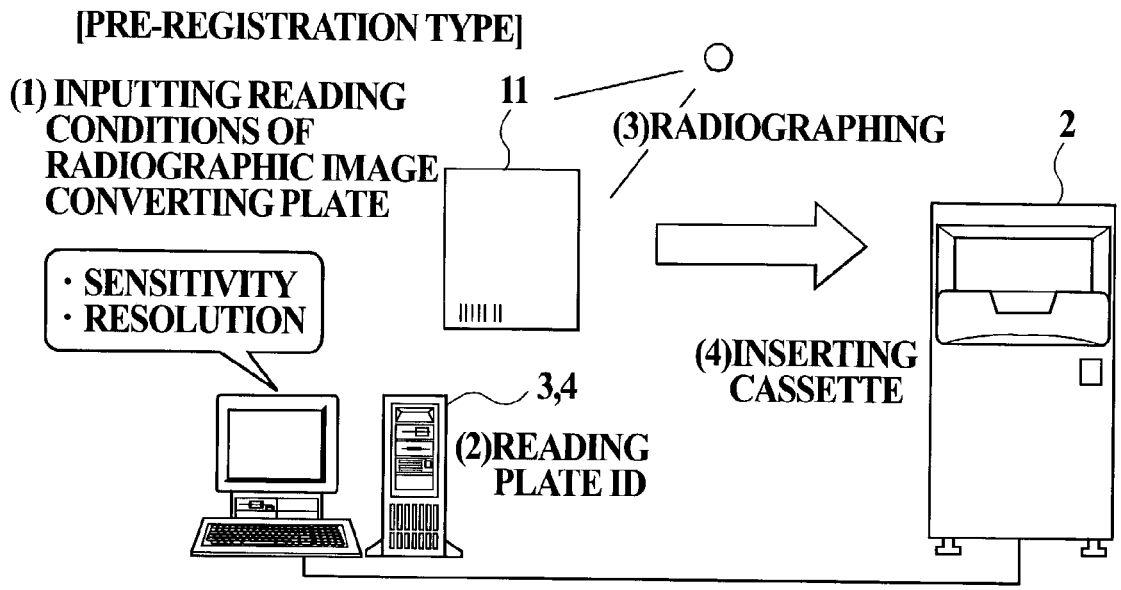
FIG. 4 is a view schematically showing a procedure of a pre-registration type.
Figure 5:
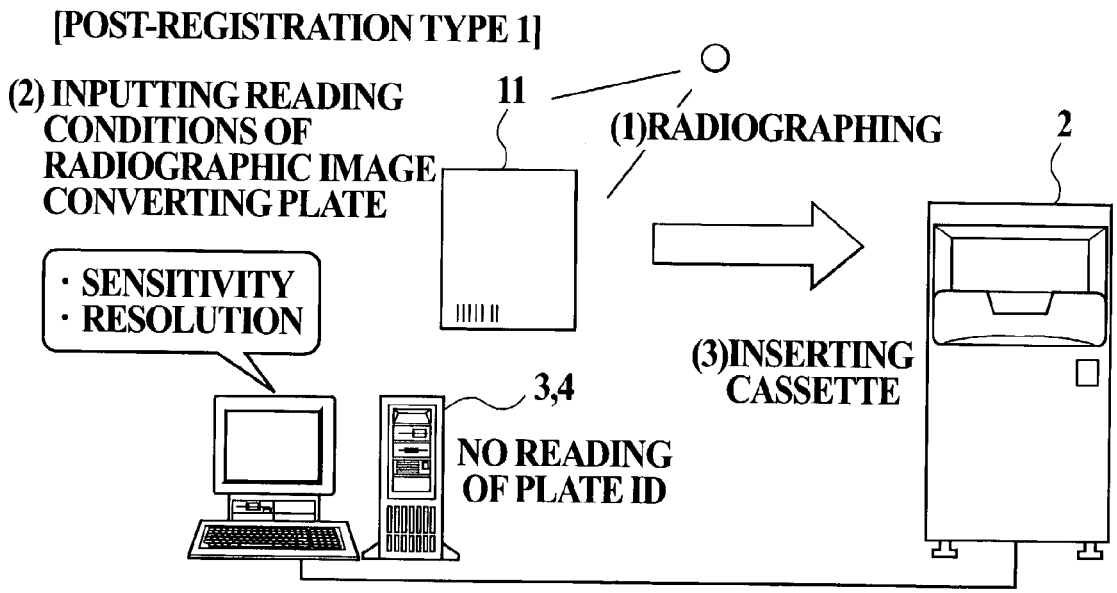
FIG. 5 is a view schematically showing a procedure of a post-registration type.
Figure 6:
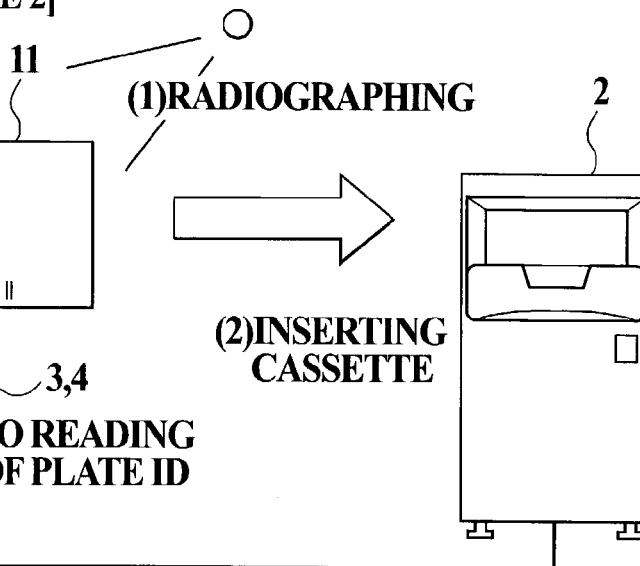
FIG. 6 is a view schematically showing a procedure of a post-registration type.
Figure 7:
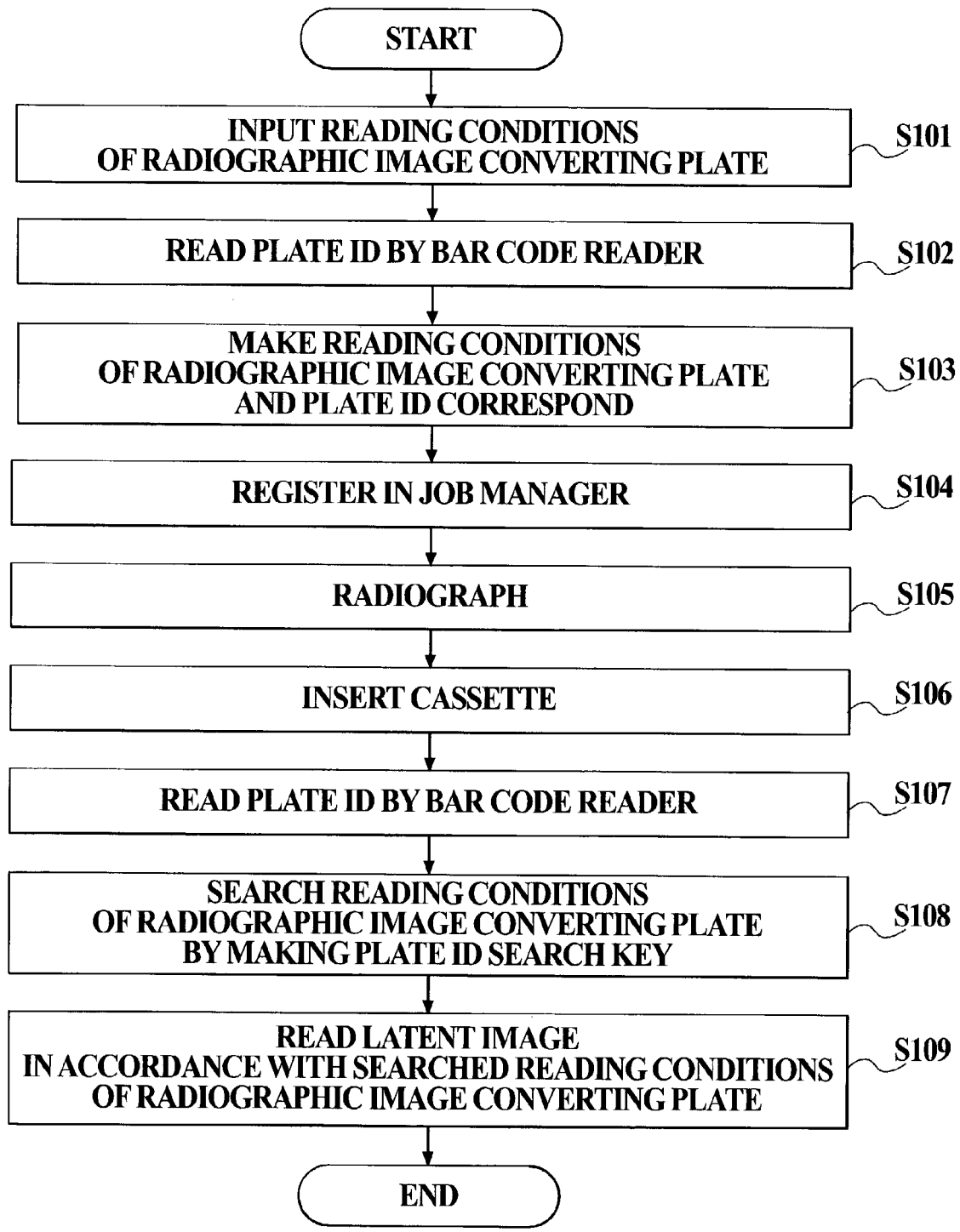
FIG. 7 is a flowchart showing an image reading procedure (pre-registration type) according to the first embodiment of the present invention.
Figure 8:
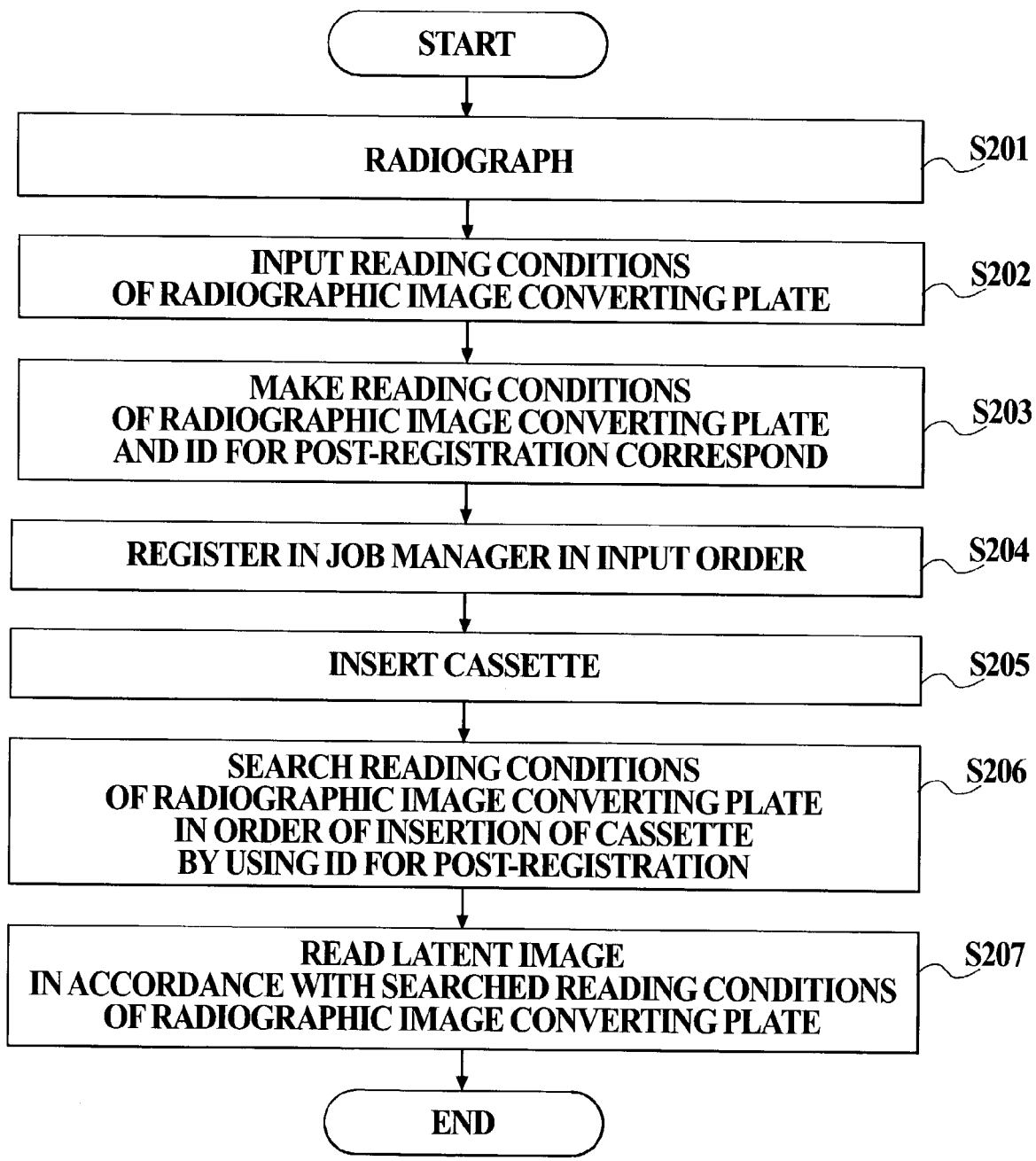
FIG. 8 is a flowchart showing an image reading procedure (post-registration type) according to the first embodiment of the present invention.

At first, an image reading apparatus (system) and method according to a first embodiment of the present invention will be explained with reference to FIGS. 1 to 8. FIG. 1 is a block diagram schematically showing a construction of an X-ray imaging system according to a first embodiment of the present invention. FIG. 2 is a block diagram schematically showing a construction in every installation place. Further, FIG. 3 is a block diagram showing a function of the image reading apparatus (reader, controller and job manager) according to the first embodiment of the present invention. Further, FIGS. 4 to 6 are views schematically showing procedures of the image reading method of the first embodiment. FIGS. 7 and 8 are their flowcharts. In addition, in the first embodiment, the case that one set of image reading apparatus is installed is explained.

As shown in FIGS. 1 and 2, in an X-ray imaging system 1 in the first embodiment, a reader 2 for reading an X-ray image from a radiographic image converting plate in which a latent image is formed by being exposed by an X-ray generating device, a controller 3 for controlling the reading of the reader 2, displaying the read image, and inputting the reading conditions of the radiographic image converting plate, a job manager 4 for storing corresponding information between the apparatus and the registration type or corresponding information between the radiographic image converting plate and the reading conditions of the radiographic image converting plate in the pre-registration or post-registration type, and for searching the reading conditions of the radiographic image converting plate corresponding to the radiographic image converting plate (hereinafter, a database comprising a storage function and searching function is called job manager), and a printer 7, a viewer 8, a patient reception terminal 9 and the like that are installed if needed are connected by a LAN 10 via a switching HUB 6. Further, although it is not shown, these devices are connected to other medical equipments by a protocol such as DICOM (Digital Image and Communication in Medicine) or the like.

In addition, hereinafter, a mode such that the reader 2 and the controller 3 are a separated will be explained. However, it may be a mode such that they are combined to constitute the image reading apparatus. Further, the job manager 4 is provided in the inside of the controller 3. However, the jog manager 4 may be connected independently to the network as one device. Further, on account of explanation, the one comprising a reading function only is called reader 2, the one comprising a display and input function, image processing function or a database function with the reader 2 is called image reading apparatus 5, and moreover, the system in which this apparatus and other equipments are connected through a network is called X-ray imaging system.

Next, the functions of the reader 2, the controller 3, and the job manager 4 included in the image reading apparatus 5 will be explained.

In the reader 2, for example, a cassette and plate control section 17 for controlling the insertion of the cassette 11 carries the cassette 11 to an identification label detector 18, and an identification label 12 stuck on the cassette 11 or the plate is read (c.f. FIGS. 4 to 6). After the label 12 is read, the radiographic image converting plate is separated from the cassette 11, and is carried to an image reading section 16. The image reading section 16 reads the latent image by scanning the radiographic image converting plate.

Further, the controller 3 comprises a display and operation section 19 for displaying and operating the order information, such as patient information, reading conditions of the radiographic image converting plate, body parts for radiographing, and the like; an identification label detector 21 for reading the identification label 12 stuck on the cassette 11 or the plate; a control section 20 for performing various image processing to the image read by the reader 2; and a storage section 22 for storing the order information and the image read by the reader 2.

Furthermore, the job manager 4 comprises a storage section 23 for storing that the controller 3 or the reader 2 is set in the pre-registration type or post-registration type, or for storing the corresponding information between the identification label ID read by the identification label detector 21 and the reading conditions of the radiographic image converting plate in case of pre-registration type, or for storing the corresponding information between the ID for post-registration and the reading conditions of the radiographic image converting plate in input order in case of post-registration type; and a search section 24 for searching the reading conditions of the radiographic image converting plate from the identification label ID or the ID for post-registration.

That is, in the image reading apparatus 5 in the first embodiment, the registration type of the controller 3 or the reader 2 can be set beforehand. The reading of the reader 2 or the control of the controller 3 is performed in accordance with the set registration type. Further, the reading conditions of the radiographic image converting plate and the like can be taken out even when either registration type is adopted.

The method for obtaining an X-ray image of a patient by using the reader 2, controller 3 and job manager 4 having the above-described construction will be explained hereafter. The pre-registration type and the post-registration type will be explained before the detail procedures are shown with reference to FIGS. 4 to 6. FIG. 4 is a view schematically showing the procedure of the pre-registration type, and FIGS. 5 and 6 are views schematically showing the procedures of the post-registration type.

As shown in FIG. 4, in case of the pre-registration type, an operator, such as radiologist or the like, inputs the reading conditions (sensitivity and resolution) of the radiographic image converting plate at the time of reading the image with the reader 2, by a display and operation section 19 of the controller 3 ((1) in FIG. 4) at first. At that time, the information (hereinafter, it is called "plate ID") of the identification label 12 stuck on the cassette 11 is read by the identification label detector 21 of the controller 3 ((2) in FIG. 4). Then, the inputted sensitivity, resolution and plate ID are sent to the job manager 4, and the above-described information are stored in the storage section 23 of the job manager 4. Thereafter, radiographing is performed by using the registered cassette 11 ((3) in FIG. 4), and the cassette 11 on which a latent image is formed is inserted into the reader 2 ((4) in FIG. 4). The plate ID of the cassette 11 is read by the identification label detector 18 built in the reader 2, and is sent to the job manager 4. In the job manager 4, the reading conditions of the radiographic image converting plate corresponding to the plate ID are searched by the search section 24 and then sent back to the reader 2. Then, the reader 2 reads the image on the basis of the obtained reading conditions of the radiographic image converting plate.

On the other hand, as shown in FIG. 5, in case of the post-registration type, an operator, such as radiologist or the like, performs radiographing at first ((1) in FIG. 5), and thereafter, inputs the reading conditions (sensitivity and resolution) of the radiographic image converting plate at the time of reading the image with reader 2, by the display and operation section 19 of the controller 3 ((2) in FIG. 5). Here, in case of the post-registration type, reading of the plate ID is not performed. In the job manager 4, the ID for post-registration and the reading conditions of the radiographic image converting plate are made to correspond, and are registered in input order. Then, the cassette 11 on which a latent image is formed is inserted into the reader 2 ((3) in FIG. 5). In the job manager 4, the reading conditions of the radiographic image converting plate are searched by the search section 24 in accordance with the correspondence between input order of the reading conditions of the radiographic image converting plate and insertion order of the cassette 11, and are sent to the reader 2. Then, the reader 2 reads the image on the basis of the obtained reading conditions of the radiographic image converting plate.

The above-described procedure is a general procedure of post-registration type. However, it can also be considered that the order of input of the reading conditions of the radiographic image converting plate and insertion of the cassette 11 may become reverse. For example, as shown in FIG. 6, an operator, such as radiologist or the like, performs radiographing at first ((1) in FIG. 6), and thereafter, inserts the cassette 11 on which a latent image is formed into the reader 2 ((2) in FIG. 6). In case that the reading conditions (sensitivity and resolution) of the radiographic image converting plate at the time of reading the image with the reader 2 is inputted by the display and operation section 19 of the controller 3 ((3) in FIG. 6) thereafter, since the reading conditions of the radiographic image converting plate is not determinate at the time of insertion of the cassette 11, the reader 2 is made to standby as it is. Then, when the reading conditions of the radiographic image converting plate are inputted from the controller 3 and the reading conditions of the radiographic image converting plate corresponding to the cassette 11 are registered, the reading conditions of the radiographic image converting plate are searched by the search section 24 in accordance with the correspondence between the input order of the reading conditions of the radiographic image converting plate and the insertion order of the cassette 11, and are sent to the reader 2. Then, the reader 2 reads the image on the basis of the obtained reading conditions of the radiographic image converting plate.

Thus, the order of input of the reading conditions by the controller 3 and insertion of the cassette 11 into the reader 2 is different between the pre-registration type and the post-registration type. Further, in the pre-registration type, the plate ID and the reading conditions of a radiographic image converting plate are made to correspond (by connecting section), and the reading conditions of the radiographic image converting plate are searched by using the plate ID. On the contrary, in the post-registration type, reading of the plate ID is not performed, but the ID for post-registration and the reading conditions of the radiographic image converting plate are made to correspond (by connecting section) and are registered in input order. Then, the reading conditions of the radiographic image converting plate are searched in accordance with the input order of the reading conditions of the radiographic image converting plate and the insertion order of the cassette 11. Thus, since an image is read in different way between the pre-registration type and the post-registration type, the image reading apparatus in earlier technology cannot respond to both registration types.

Then, in the first embodiment, the job manager 4 comprises a storage section 23 for recording corresponding information between each device and each registration type, and corresponding information between the ID in each registration type (plate ID or ID for post-registration) and the reading conditions of a radiographic image converting plate; and a search section 24 for searching by making the plate ID a key, or for searching in accordance with the correspondence between the input order of the reading conditions of the radiographic image converting plate and the insertion order of the cassette 11. Thereby, the registration type of each device is specified with reference to the corresponding information stored in the storage section 23 of the job manager 4 at the time of start-up of the system, so that it is possible to search the reading conditions of the radiographic image converting plate according to each registration type.

Hereinafter, a concrete procedure in each registration type will be explained in detail with reference to flowcharts in FIGS. 7 and 8. FIG. 7 shows an image reading procedure in case that the controller 3/reader 2 are set to pre-registration type. FIG. 8 shows an image reading procedure in case that the controller 3/reader 2 are set to post-registration type. In addition, in the following explanation, a barcode is used as an identification label 12 of a cassette 11, and barcode readers are connected to the controller 3 and reader 2, respectively. However, other identifying methods can be used.

At first, the case of setting to the pre-registration type will be explained with reference to FIG. 7. In Step S101, the reading conditions (sensitivity and resolution) of a radiographic image converting plate are inputted by the display and operation section 19 of the controller 3. Here, there is a case that the reading conditions of the radiographic image converting plate are obtained from a host system, such as X-ray information system or the like. Thereafter, in Step S102, the barcode stuck on the cassette 11 or the plate is read by using the barcode reader (identification label detector 21) connected to or built in the controller 3, and the plate ID including information, such as kind, size or the like of the cassette 11, are read.

Next, in Step S103, the controller 3 sends the inputted reading conditions of the radiographic image converting plate and the plate ID read by the barcode to the job manager 4. The job manager 4 makes the plate ID and the reading conditions of the radiographic image converting plate correspond, and stores them in the storage section 23 in Step S104. Here, mechanisms of registering and searching data of the existing database can be applied as the job manager 4.

Next, in Step S105, an X-ray is exposed to a subject and the cassette 11 from an X-ray generating device according to a well-known method, and body parts for radiographing of the subject are recorded on the radiographic image converting plate built in the cassette 11 as a latent image. Here, the image recording is not limited to an X-ray generating device. It may include image recording according to, for example, magnet, ultrasonic wave or the like.

Next, in Step S106, the cassette 11 to which the X-ray is exposed is inserted into a slot of the reader 2. Then, in Step S107, the reader 2 detects the barcode stuck on the cassette 11 or the plate and reads the plate ID by using the barcode reader (identification label detector 18) built therein.

Then, in Step S108, the reader 2 sends the read plate ID to the job manager 4. The job manager 4 searches the reading conditions of the radiographic image converting plate corresponding to the plate ID from the data recorded in the storage section 23 by making the plate ID a search key, and sends them to the reader 2. In Step S109, the reader 2 reads the latent image by using these reading conditions of the radiographic image converting plate.

Next, the procedure of the case of setting to the post-registration type (the post-registration type 1 in FIG. 5) will be explained with reference to FIG. 8. At first, in Step S201, an X-ray is exposed to a subject and the cassette 11 from an X-ray generating device according to a well-known method, and body parts for radiographing of the subject are recorded on a radiographic image converting plate built in the cassette 11 as a latent image.

Next, in Step S202, the reading conditions (sensitivity and resolution) of the radiographic image converting plate are inputted by the display and operation section 19 of the controller 3. Here, there is a case that the reading conditions of the radiographic image converting plate are obtained from a host system, such as hospital information system, X-ray information system or the like.

Thereafter, in Step S203, the controller 3 sends the inputted reading conditions of the radiographic image converting plate and the ID for post-registration set beforehand to the job manager 4. The job manager 4 makes the ID for post-registration and the reading conditions correspond, and stores them in the storage section 23 in Step S204 by taking the input order into consideration.

Next, in Step S205, when the cassette 11 to which the X-ray is exposed is inserted into the slot of the reader 2, in Step S206, the job manager 4 searches the reading conditions of the radiographic image converting plate by corresponding the input order of the reading conditions of the radiographic image converting plate to the insertion order of the cassette 11 from the data recorded in the storage section 23, by using the ID for post-registration, and sends them to the reader 2. In Step S207, the reader 2 reads the latent image by using these reading conditions of the radiographic image converting plate.

Thus, in the image reading apparatus 5 of the first embodiment, the job manager 4 comprises a storage section 23 for recording corresponding information between each device and each registration type, and corresponding information between the ID in each registration type (plate ID or ID for post-registration) and the reading conditions of a radiographic image converting plate; and a search section 24 for searching by making the plate ID a key, or for searching in accordance with the input order of the reading conditions of the radiographic image converting plate and the insertion order of the cassette 11. Then, the registration type of each device is set with reference to the corresponding information stored in the storage section 23 of the job manager 4 at the time of start-up of the system, so that it becomes possible to read out the reading conditions of the radiographic image converting plate corresponding to the cassette 11 by using the ID (plate ID or ID for post-registration) even though it is a case that it is set to either of the registration types. Thereby, the registration type can be selected appropriately in accordance with the installation mode, using condition or the like of the controller 3/reader 2.

[Second Embodiment]

Figure 9:
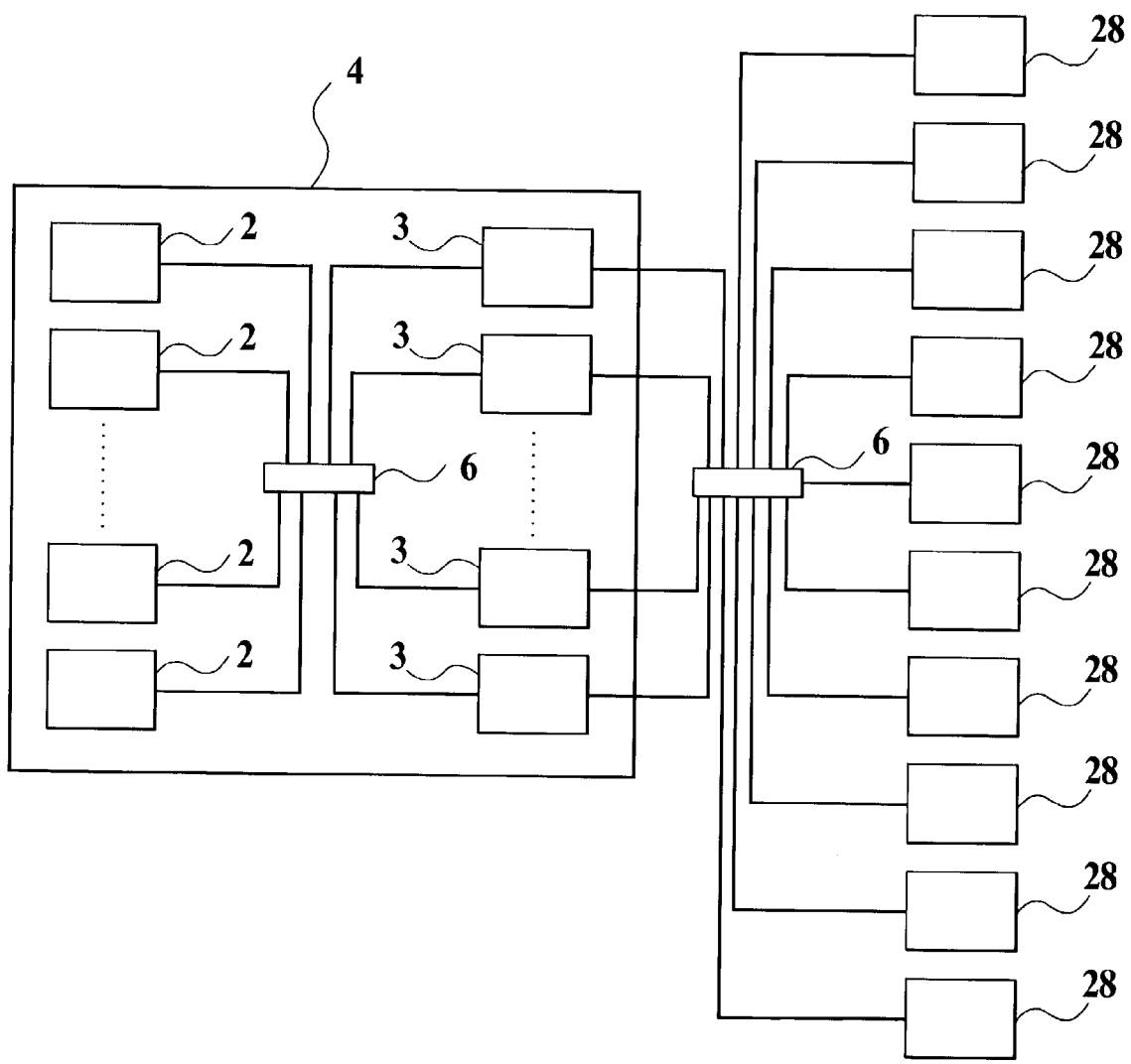
FIG. 9 is a block diagram schematically showing a construction of an X-ray imaging system (expanded system) according to a second embodiment of the present invention.
Figure 10:
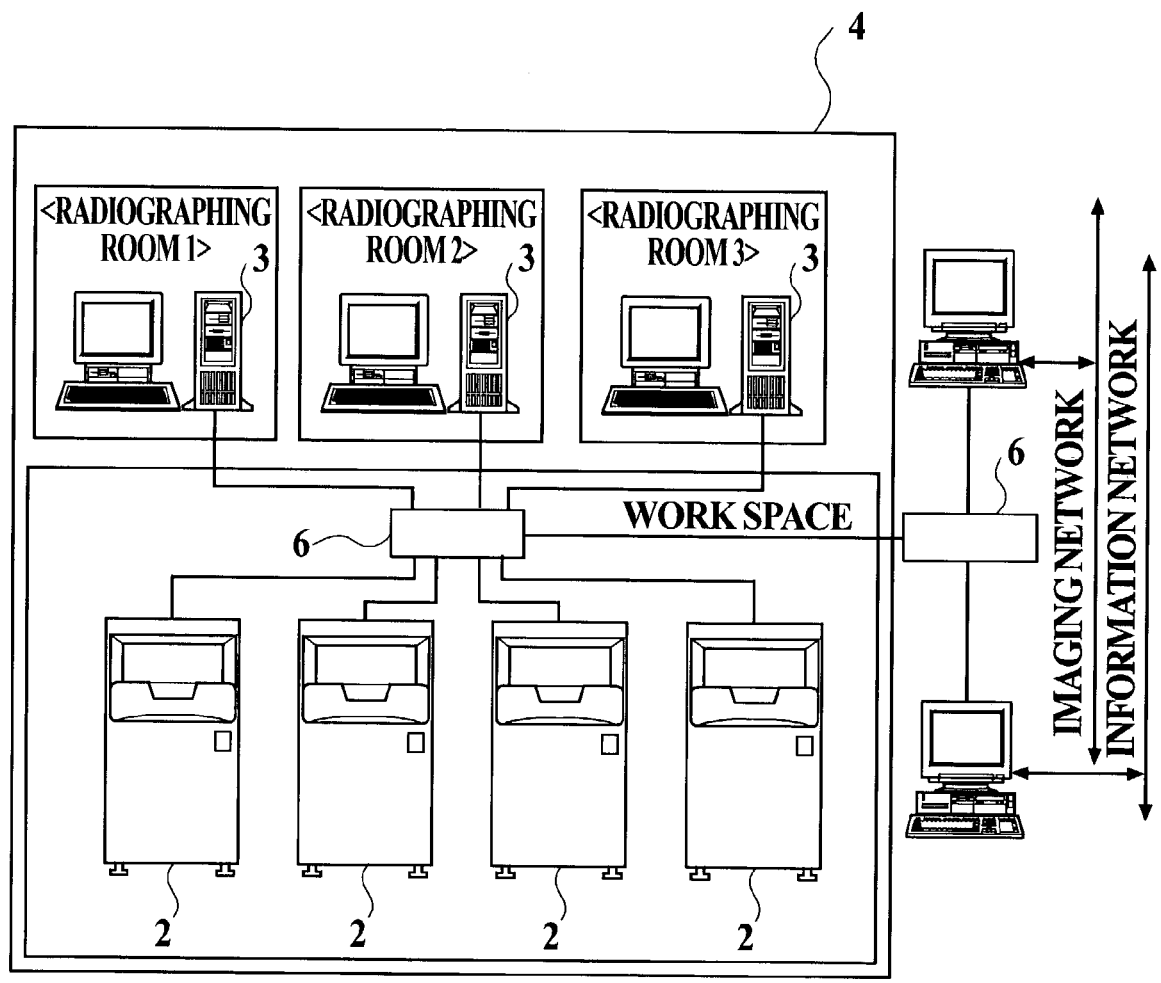
FIG. 10 is a block diagram schematically showing a construction of the X-ray imaging system (expanded system) according to the second embodiment of the present invention in every installation place.
Figure 11:
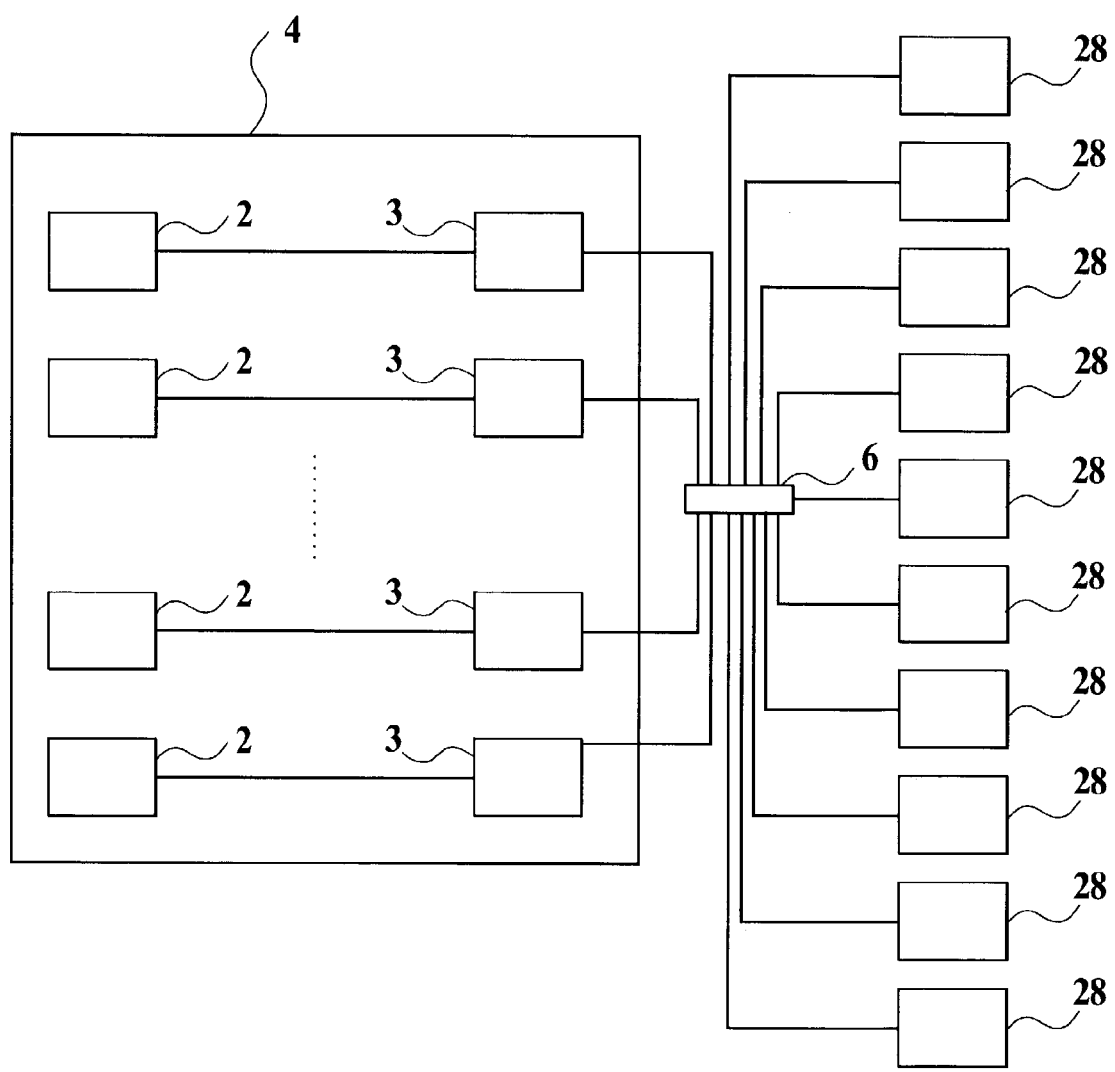
FIG. 11 is a block diagram schematically showing a construction of an X-ray imaging system (distributed system) according to the second embodiment of the present invention.
Figure 12:
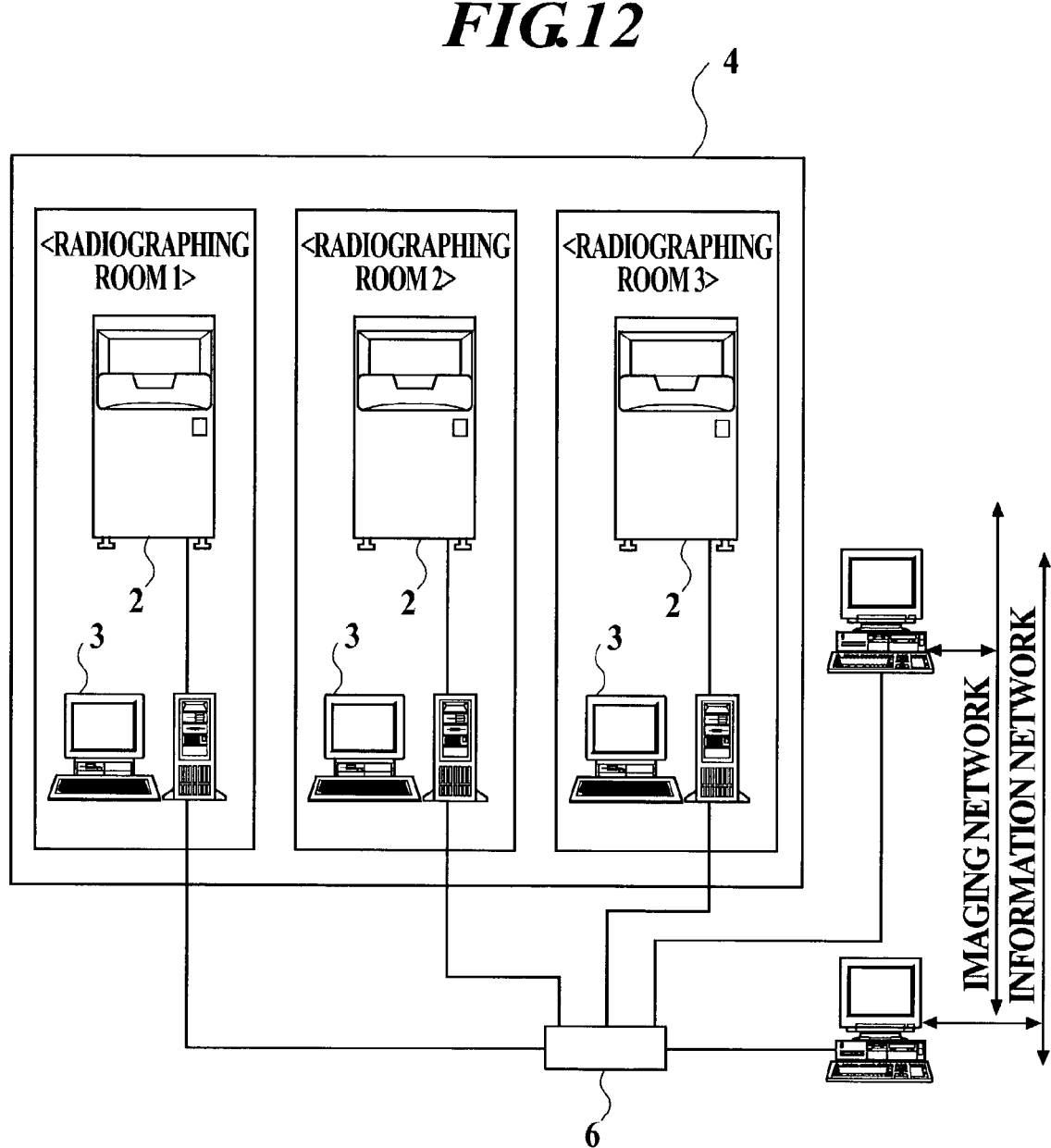
FIG. 12 is a block diagram schematically showing a construction of the X-ray imaging system (distributed system) according to the second embodiment of the present invention in every installation place.
Figure 13:
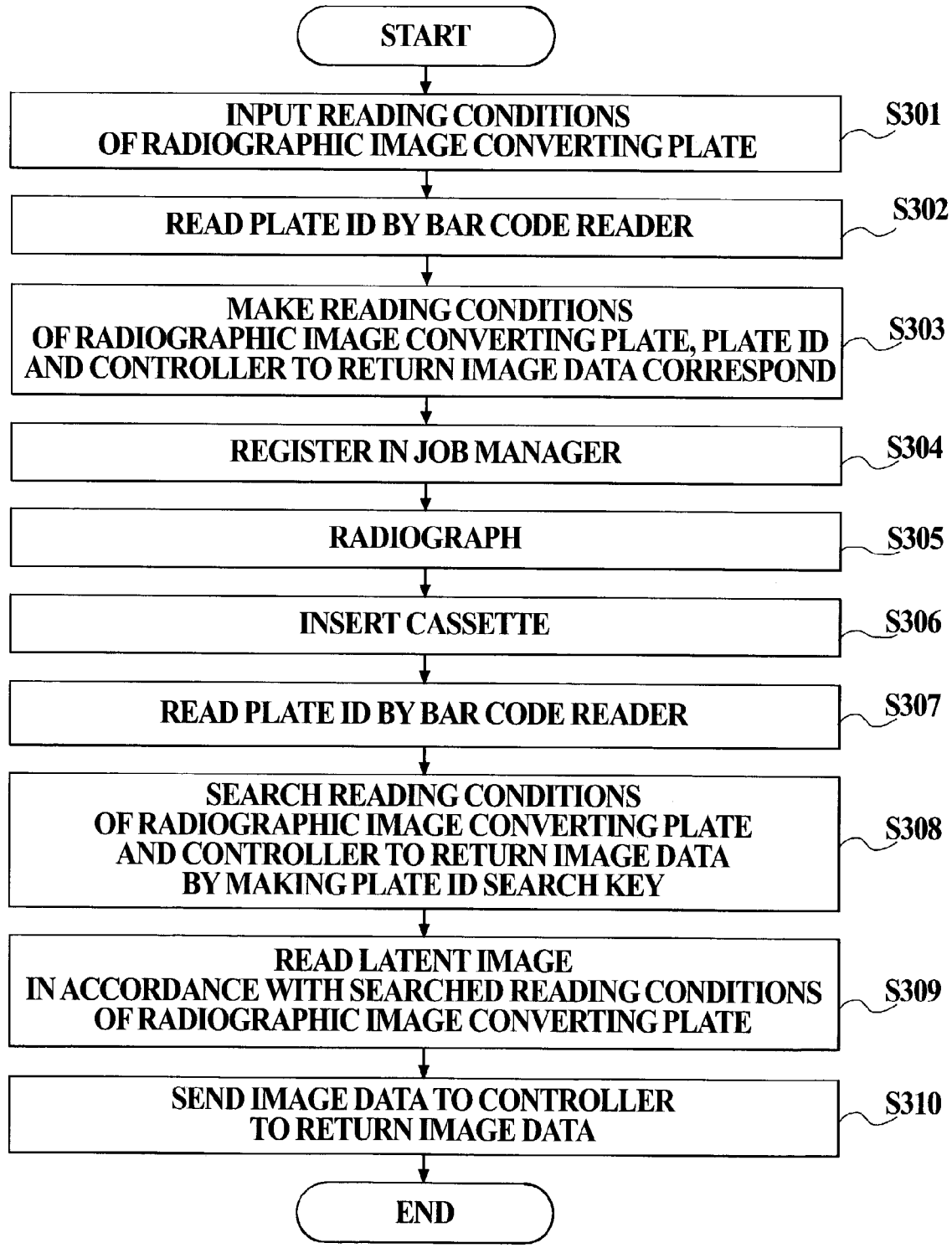
FIG. 13 is a flowchart showing an image reading procedure (pre-registration type) according to the second embodiment of the present invention.
Figure 14:
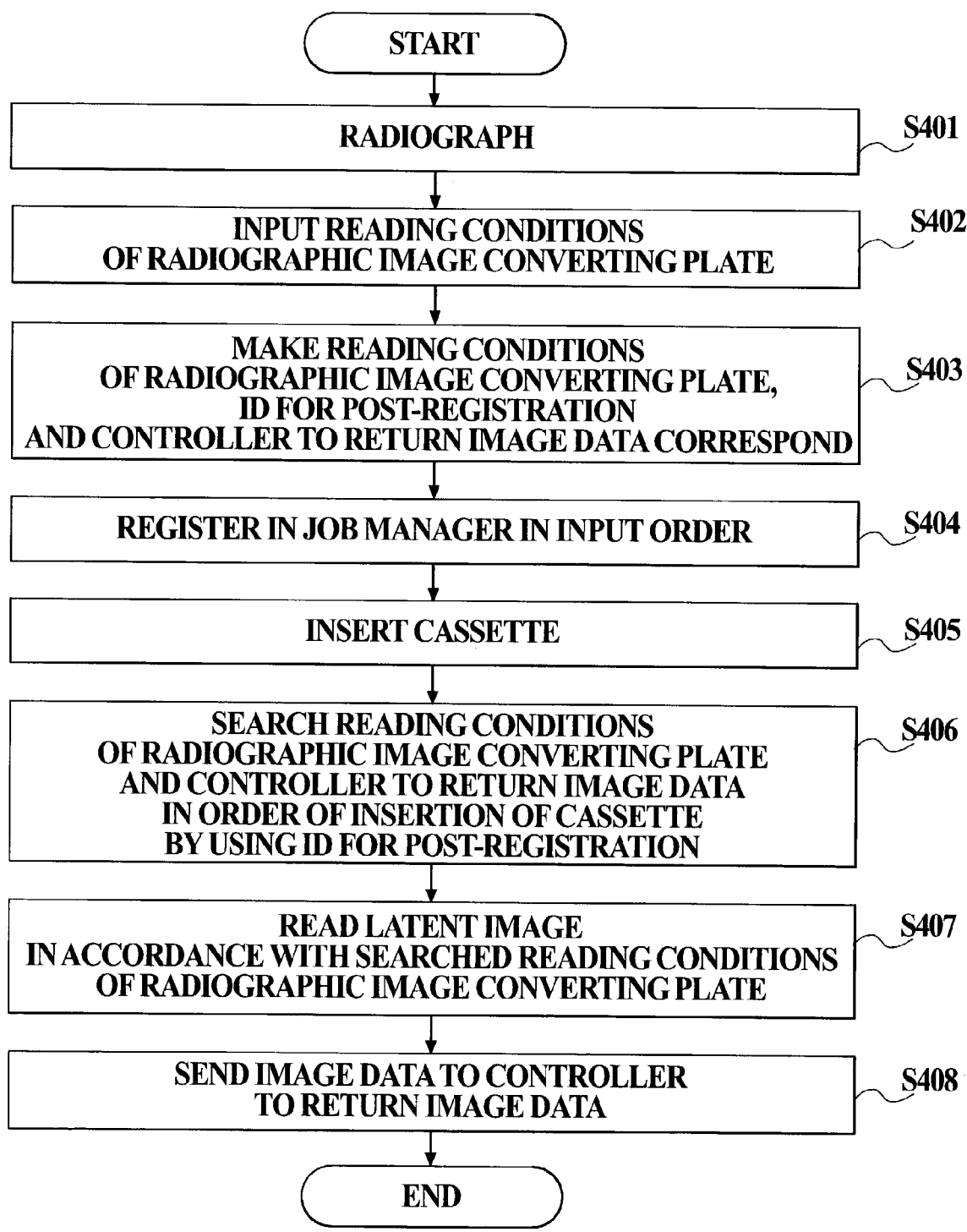
FIG. 14 is a flowchart showing an image reading procedure (post-registration type) according to the second embodiment of the present invention.

Next, an image reading apparatus (system) and method according to a second embodiment of the present invention will be explained with reference to FIGS. 9 to 14. FIGS. 9 and 10 are block diagrams schematically showing a construction of an X-ray imaging system (expanded system) according to the second embodiment of the present invention. FIGS. 11 and 12 are block diagrams schematically showing a construction of an X-ray imaging system (distributed system) according to the second embodiment of the present invention. Further, FIGS. 13 and 14 are flowcharts showing image reading procedures of the image reading method. In addition, in the second embodiment, a system such that a plurality of image reading apparatuses (readers and controllers) are installed is described.

That is, in the above-mentioned first embodiment, a construction such that one set of image reading apparatus 5 (a reader 2, controller 3 and job manager 4) is installed is shown. However, in the image reading method of the present invention, since the pre-registration type and the post-registration type can be used properly arbitrarily, it can be applied also to a mode that a plurality of readers and a plurality of controllers are connected.

For example, as shown in FIGS. 9 and 10, it can be applied to a system such that the controllers 3 are installed in a plurality of radiographing rooms, respectively, and a plurality of readers 2 are installed so as to be concentrated in a workspace which is different from the radiographing rooms, and moreover, printers, viewers 28 and the like are connected by LAN through a switching HUB 6 (this mode is called "expanded system"). For the expanded system such that the readers 2 and controllers 3 are constructed by m:n (in FIG. 10, the case that four readers 2 and three controllers 3 are connected is shown as an example), the pre-registration type is generally adopted.

Hereafter, a procedure for reading an image according to pre-registration type in the expanded system will be explained with reference to the flowchart in FIG. 13. At first, similarly to FIG. 7 in the above-mentioned first embodiment, in Step S301, the reading conditions (sensitivity and resolution) of a radiographic image converting plate are inputted by the display and operation section 19 of an arbitrary controller 3. Thereafter, in Step S302, the barcode stuck on the cassette 11 or the plate is read by using the barcode reader (identification label detector 21) connected to or built in the controller 3, and the plate ID including information, such as kind, size or the like of the cassette 11, are read.

Next, in Step S303, the controller 3 sends the inputted reading conditions of the radiographic image converting plate and the plate ID read by the barcode to the job manager 4. The job manager 4 makes the plate ID and the reading conditions of the radiographic image converting plate correspond. At that time, the job manager 4 further adds specifying information of a controller 3 to return the image data so as to make it correspond, and stores them in the storage section 23 in Step S304.

The specifying information of the controller 3 to return the image data can be added automatically by the controller 3 when the reading conditions of the radiographic image converting plate and the plate ID are sent. In this case, the controller 3 by which the reading conditions of the radiographic image converting plate are inputted becomes the controller 3 to return the image data. Further, the image data can be sent to a controller 3 different from the controller 3 for inputting the reading conditions. In this case, an operator may input the information to specify the controller to return the image data when inputting the reading conditions of the radiographic image converting plate.

Hereafter, similarly to the first embodiment, in Step S305, an X-ray is exposed to a subject and the cassette 11 from an X-ray generating device according to a well-known method, and body parts for radiographing of the subject are recorded on the radiographic image converting plate built in the cassette 11 as a latent image. In Step S306, the cassette 11 to which the X-ray is exposed is inserted into a slot of a reader 2. Then, in Step S307, the reader 2 detects the barcode and reads the plate ID by using the barcode reader built therein.

Then, in Step S308, the reader 2 sends the read plate ID to the job manager 4. The job manager 4 searches the reading conditions of the radiographic image converting plate corresponding to the plate ID from the data recorded in the storage section 23 by making the plate ID a search key and extracts the specifying information of the controller 3 to return the image data, and sends them to the reader 2.

Thereafter, in Step S309, the reader 2 reads the latent image by using these reading conditions of the radiographic image converting plate, and sends the read image data to the controller 3 to return the image data in Step S310. In the controller 3 which has received the image data, a predetermined image processing is performed to the image data in accordance with the direction of the operator so as to form an image for diagnosing, and thereby, a diagnosis is made.

Further, as shown in FIGS. 11 and 12, for a system such that the readers 2 and controllers 3 are installed in each of the plurality of radiographing rooms so as to be paired with each other (that is, the readers 2 and controllers 3 are constructed by 1:1) and each controller 3 is connected by LAN through a switching HUB 6 (such a mode is called "distributed system"), the post-registration type can also be adopted.

A procedure for reading an image according to such a post-registration type in the distributed system will be explained with reference to the flowchart in FIG. 14. At first, similarly to FIG. 8 in the above-mentioned first embodiment, in Step S401, an X-ray is exposed to a subject and the cassette 11 from an X-ray generating device according to a well-known method, and body parts for radiographing of the subject are recorded on a radiographic image converting plate built in the cassette 11 as a latent image. Thereafter, in Step S402, the reading conditions (sensitivity and resolution) of the radiographic image converting plate are inputted by the display and operation section 19 of an arbitrary controller 3 Thereafter, in Step S403, the controller 3 sends the inputted reading conditions of the radiographic image converting plate and the ID for post-registration set beforehand to a job manager 4. The job manager 4 makes the ID for post-registration and the reading conditions correspond. At that time, in the second embodiment, the job manager 4 further adds specifying information of a controller 3 to return the image data so as to make it correspond, and stores them in the storage section 23 in Step S404 by taking the input order into consideration.

Thereafter, similarly to the first embodiment, in Step S405, when the cassette 11 to which the X-ray is exposed is inserted into a slot of a reader 2, in Step S406, the job manager 4 searches the reading conditions of the radiographic image converting plate by corresponding the input order of the reading conditions of the radiographic image converting plate to the insertion order of the cassette 11 from the data recorded in the storage section 23, by using the ID for post-registration and extracts the specifying information of the controller 3 to return the image data together with the reading conditions of the radiographic image converting plate, and sends them to the reader 2.

Thereafter, in Step S407, the reader 2 reads the X-ray image from the radiographic image converting plate by using these reading conditions of the radiographic image converting plate. Then, in Step S408, the read image data is sent to the controller 3 to return the image data. In the controller 3 which has received the image data, a predetermined image processing is performed to the image data in accordance with the direction of the operator so as to form an image for diagnosing, and thereby, a diagnosis is made.

Thus, in the image reading apparatus 5 of the second embodiment, the post-registration type can also be used in a mode that a plurality of readers 2 and controllers 3 are connected.

As described above, in the embodiments of the present invention, the image reading apparatus 5 comprises a reader 2 for reading image data from a radiographic image converting plate on which a radiographic image is recorded as a latent image; a controller 3 for inputting reading conditions of the radiographic image converting plate and for controlling reading of the reader 2; a job manager 4 having a storage section 23 for storing correspondence between each device and registration type or correspondence between the ID in pre-registration or post-registration and the reading conditions, and a search section 24 for searching by using a predetermined key. The registration type of each device is set beforehand. In case of pre-registration, the radiographing conditions are searched by making a plate ID a key, and in case of post-registration, the radiographing conditions are searched from the correspondence between the input order of ID for post-registration and the radiographing conditions, and the insertion order of a cassette 11. Thereby, it can correspond to either registration type.

Figure 15:
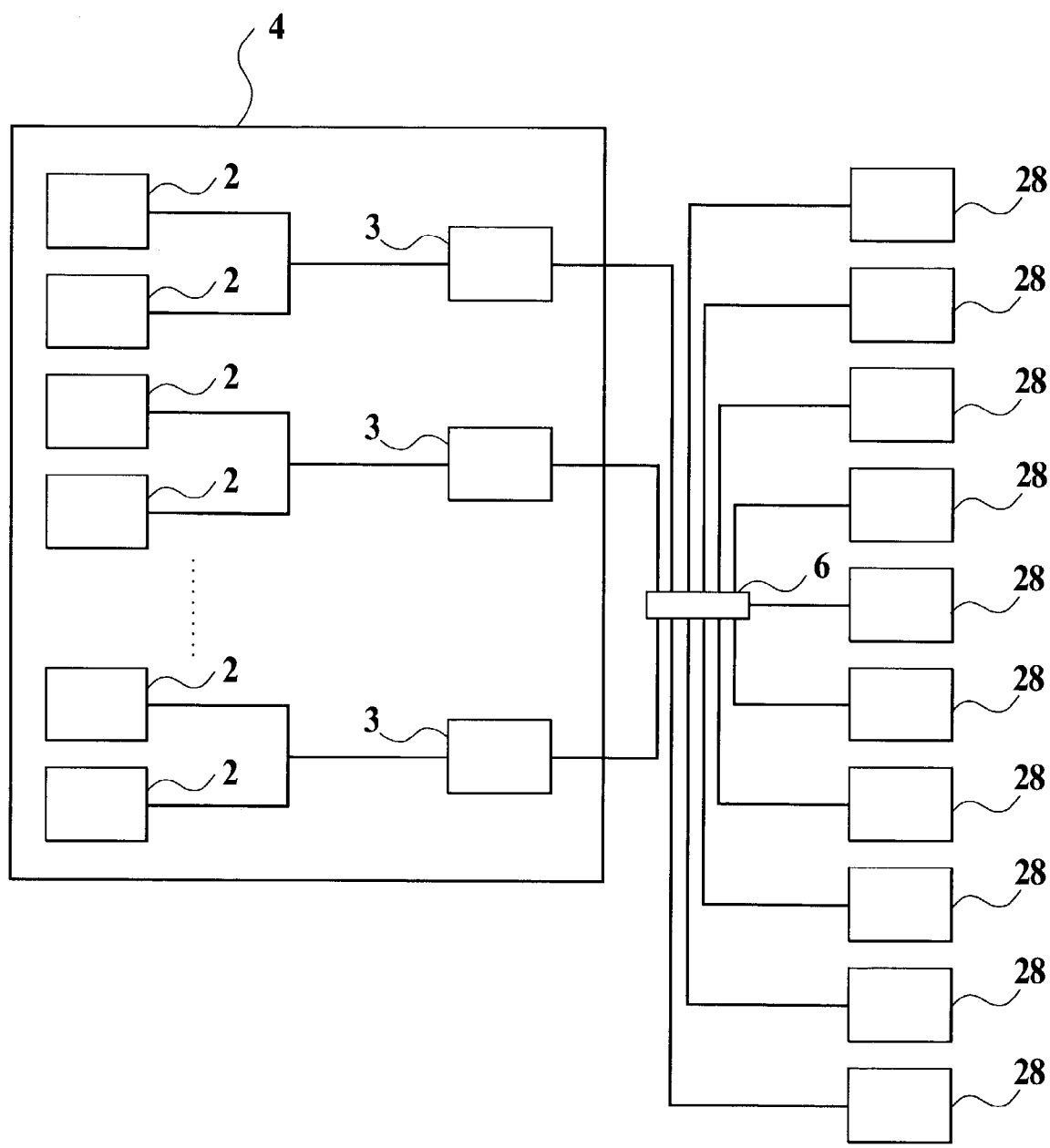
FIG. 15 is a block diagram schematically showing a construction of an X-ray imaging system (distributed system) according to a modified embodiment of the present invention.

In the above, the embodiments of the present invention are explained. However, it is needless to say that the present invention is not limited to such embodiment, but various modifications are possible in a range within the scope of the present invention. In the distributed system adopting the post-registration type according to the second embodiment, the case such that the readers 2 and controllers 3 are installed by 1:1 is explained. However, the present invention is not limited to this. For example, the readers 2 and controllers 3 may be installed by 2:1 as shown in FIG. 15.

Figure 16:
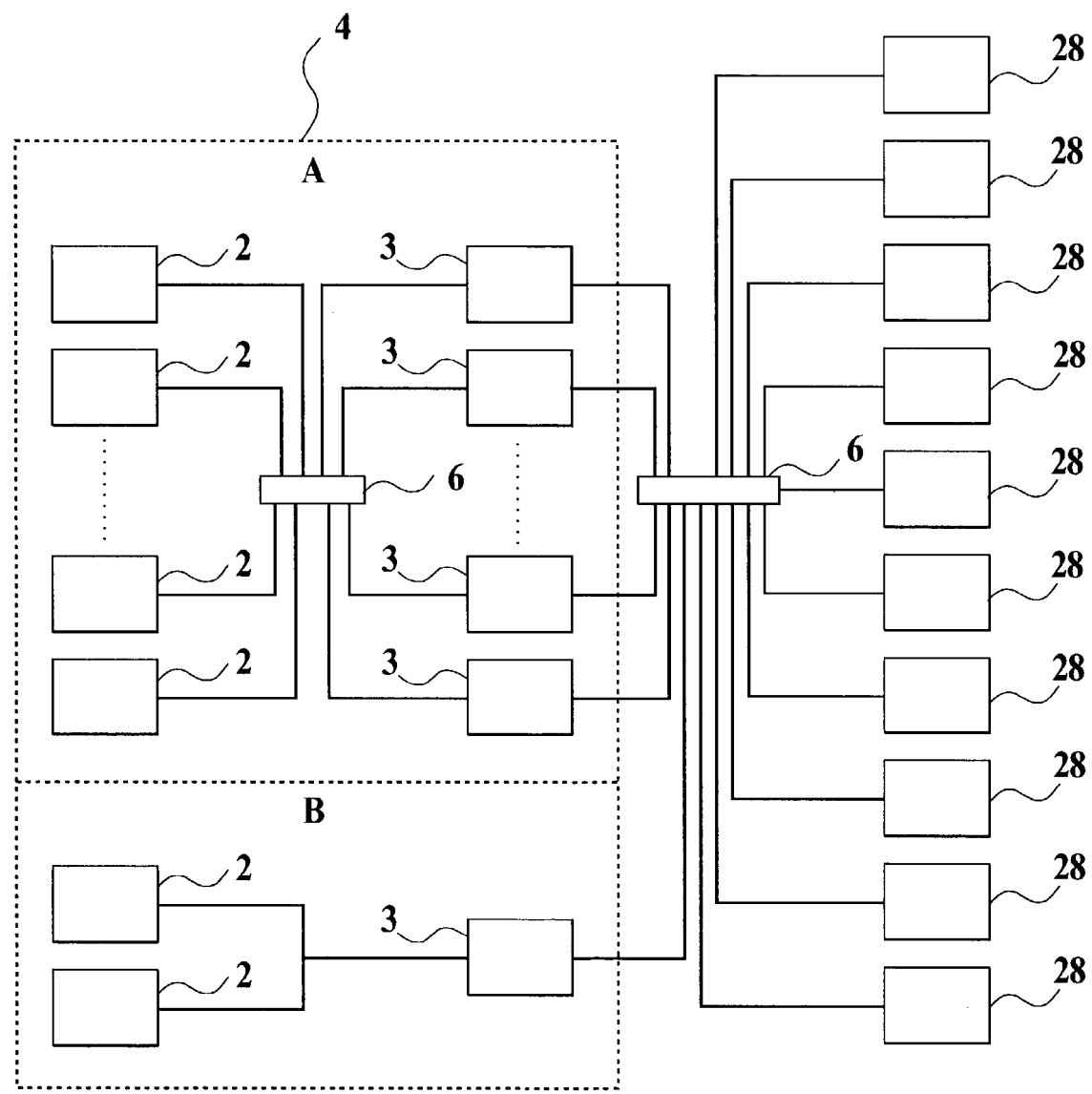
FIG. 16 is a block diagram schematically showing a construction of an X-ray imaging system (coexistence of expanded system and distributed system) according to a modified embodiment of the present invention.
Figure 17:
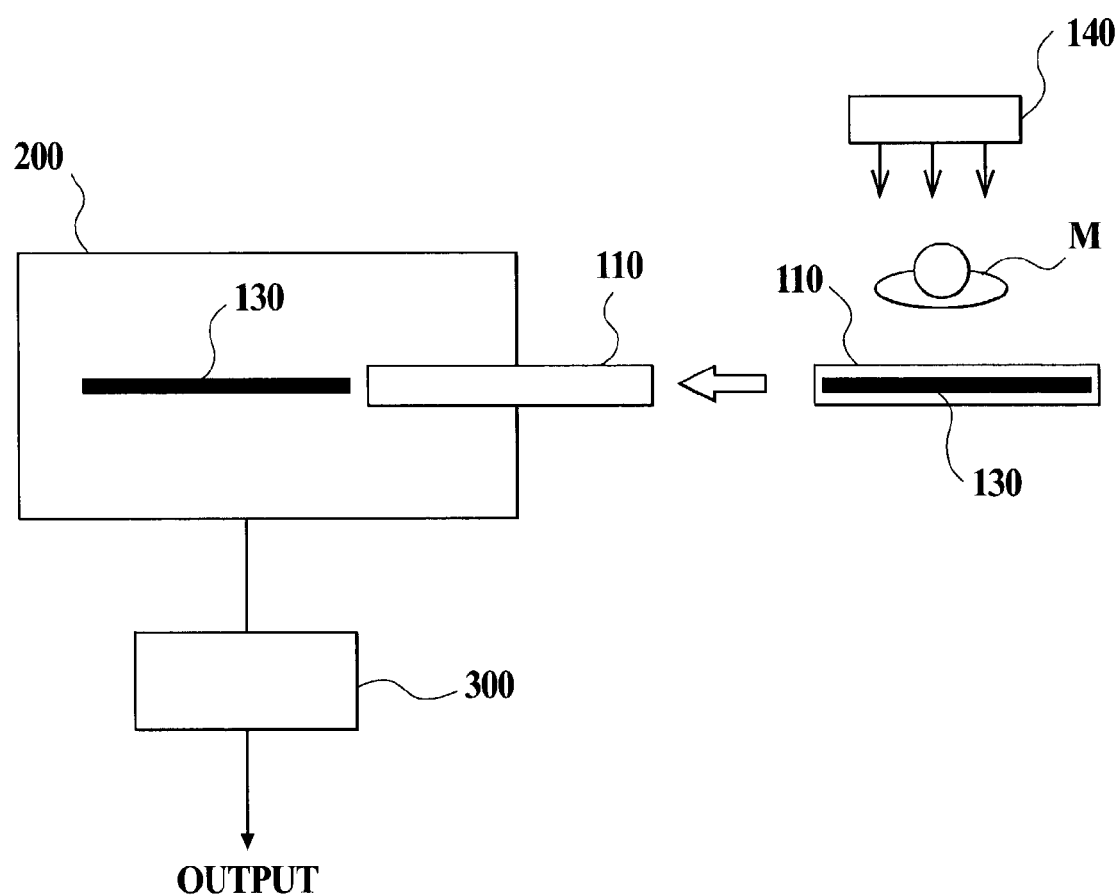
FIG. 17 is a view showing a construction of an X-ray image radiographing system in earlier technology.

Further, in the above-mentioned embodiments, the modes adopting pre-registration type and post-registration type, respectively, are explained individually. However, the present invention is not limited to these. It may be a mode that the pre-registration type and the post-registration type are coexisting such that a part of controllers 3/readers 2 is operated according to the post-registration type in the expanded system, or a part of controllers 3/readers 2 is operated according to the pre-registration type in the distributed system. An example is shown in FIG. 16. In FIG. 16, the pre-registration type is adopted in the portion A, and the post-registration type is adopted in the portion B.

According to such a construction, for example, in a hospital or the like, the portion A may be utilized as a general radiographing room, so that many radiologists can perform radiographing of many patients according to the pre-registration type, and on the contrary, the portion B may be utilized as an operating room or emergency room or the like, so that particular radiologists can perform prompt radiographing in case of emergency or the like according to the post-registration type.

Moreover, in the above-described first and second embodiments, in case of the post-registration type, the reading conditions of the radiographic image converting plate and the ID for post-registration set beforehand are made to correspond, and stored in the storage section 23 by taking the input order into consideration. Then, the reading conditions are searched by corresponding the input order of the reading conditions of the plate to the insertion order of the cassette 11. According to this type, it is effective particularly in an emergency or the like, since the time for reading the plate ID can be shortened. However, the present invention is not limited to this. For example, in Step S202 in FIG. 8 of the first embodiment, the plate ID may be read by reading the barcode stuck on the cassette 11 or the plate while the reading conditions is inputted by the controller 3. At the same time, a post-registration index (second registration type index) is added to the plate ID. Then, in Step S203, the reading conditions of the radiographic image converting plate and the plate ID are made to correspond, and in Step S204, they are stored in a folder for post-registration (second saving section) in the storage section, which is different from that for pre-registration, according to the addition of the post-registration index. Then, in Step S206, when the cassette 11 is inserted into the reader 2, the plate ID is read, and the reading conditions of the plate may be searched from the folder for post-registration by making the plate ID a search key. Needless to say, this can also be applied to the second embodiment.

In this case, particularly, in the case that the readers 2 and controllers 3 are not installed by 1:1 (for example, installed by 2:1 as shown in FIG. 15) or the like, since it is not required to take the input order of reading conditions, insertion order of cassette 11, or the like, into consideration, the relation between the radiographic image converting plate and its processing conditions (reading conditions) among devices adopting the post-registration type will be hardly mistaken. Therefore, it is enormously preferable. Further, even though the plate ID is used in this case as the same as the pre-registration type, since the plate ID is stored in a folder different from that of the pre-registration type, it will not be mistaken for the pre-registration type. Therefore, it is effective also in a mode such that the pre-registration type and the post-registration type are coexisting, for example, as shown in FIG. 16.

According to the present invention, since the registration type (pre-registration type, post-registration type) can be set or changed appropriately by using the same devices (e.g. reader, controller and the like), changing from pre-registration to post-registration or from post-registration to pre-registration can be carried out easily. That is, since selection of pre-registration type and post-registration type is not carried out by system construction according to connecting the system-configuring devices, including readers, controllers and the like, by hardware, the selection is easy. Moreover, changing from pre-registration to post-registration, from post-registration to pre-registration, or the like, after the system is started can be carried out easily.

The entire disclosure of Japanese Patent Application No. 2002-023351 filed on Jan. 31, 2002 including specification, claims, drawings and summary are incorporated herein by reference in its entirety.

What is claimed is:

1. An image reading system comprising:
   a plurality of image reading apparatuses, each of the image reading apparatus having a reading device reading image information from a containing member in which a recording medium having a radiographic image thereon, a control device setting a reading condition of the containing member, and an identification detector detecting ID information given to the containing member or the recording medium;
   a selecting section selecting a first registration type or a second registration type of the each image reading apparatus, the first registration type being for registering a correspondence between the reading condition and the containing member or the recording medium before image recording and the second registration type being for registering the correspondence after the image recording;
   an ID giving section for giving ID information for the second registration type to the containing member or the recording medium;
   a first saving section storing the reading condition of the each containing member corresponding to the detected ID information by the identification detector;
   a second saving section storing the reading condition of the each containing member corresponding to the given ID information by the ID giving section;
   a search section searching the reading condition, the search section searching the reading condition stored in the first saving section corresponding to the detected ID information by the identification detector when the first registration type is selected, and the search section searching the reading condition stored in the second saving section corresponding to the given ID information by the ID giving section when the second registration type is selected; and
   a control section controlling the reading device so as to read the image information on the basis of the reading condition searched by the search section according to the ID information.

2. The system of claim 1, further comprising:
control apparatus having a function of displaying the read image information.

3. The system of claim 1, wherein the reading device comprises a function of giving the ID information.

4. The system of claim 1, wherein each of the reading apparatus comprises a function of displaying the read image information.

5. The system of claim 1, wherein the selecting section makes the first registration type and the second registration type coexist in the image reading system.

6. The system of claim 1, wherein at least one of the control device and the ID giving section comprises a specifying section for specifying a destination to deliver the read image information.

7. The system of claim 1, wherein the radiographic image is an X-ray image.

8. The system of claim 1, wherein the ID information for the first registration type is a barcode.

9. The system of claim 1, comprising a plurality of the control devices.

10. The system of claim 9, wherein the control section makes the image reading system capable of being used by making the first registration type and the second registration type coexist.

11. The system of claim 9, wherein the reading devices and the control devices are correlated by 1:1 when the second registration type is selected.

12. The system of claim 1, wherein the ID giving section adds a second registration type index to the ID information when the second registration type is selected, and
the second saving section stores the rending condition corresponding to the ID information to which the second registration type index is added.

13. An image reading method for reading image information from a containing member in which a recording medium capable of recording a radiographic image is built, comprising:
selecting at least one of a first registration type and a second registration type, the first registration type being for registering a correspondence between the reading condition and the containing member or the recording medium before image recording and the second registration type being for registering the correspondence after the image recording; and
setting a reading condition of the containing member,
wherein when the first registration type is selected, the method comprises:
registering the reading condition and the ID information given to the containing member or the recording medium by making them correspond before the image recording a radiographic image to the recording medium;
detecting the ID information given to the containing member or the recording medium after the image recording;
searching the reading condition corresponding to the detected ID information; and
controlling reading of the image information on a basis of the reading condition corresponding to the detected ID information, and
when the second registration type is selected, the method comprises:
giving ID information to the containing member or the recording medium;
registering the reading condition and the given ID information in input order by making them a correspond before the image recording;
recording a radiographic image to the recording medium;
searching the reading condition from a correspondence between registration order of the reading condition and image reading order of the containing member; and
controlling reading of the image information on a basis of the reading condition.

14. The method of claim 13, further comprising:
adding information for specifying a device to send the read image information, when the reading condition is registered; and
sending the read image information to the specified device.

15. The method of claim 13, wherein the reading of the image information is carried out by a plurality of image reading apparatuses, and the selection of the first registration type and the second registration type is carried out on each of the image reading apparatuses.

16. The method of claim 13, wherein the reading of the image information is carried out by an image reading apparatus having a reading device for reading the image information, and a control device for setting the reading condition in the reading device,
the image reading method further comprises:
storing corresponding information between at least one of the reading device and the control device, and the first and second registration types, and
at least one of the first registration type and the second registration type is selected with reference to the corresponding information when at least one of the reading device and the control device is actuated.

17. The method of claim 13, wherein the reading condition includes information of sensitivity and resolution.

18. The method of claim 13, wherein the radiographic image is an X-ray image.

19. The method of claim 13, wherein the ID information for the first registration type is a barcode.

* * * * *